(12) United States Patent
Blaskovic et al.

(10) Patent No.: US 11,912,666 B2
(45) Date of Patent: Feb. 27, 2024

(54) SYNTHESIS OF 6-OXO-1,4,5,6-TETRAHYDROPYRIDIZIN-3-CARBOXYLIC ACID

(71) Applicant: Millennium Enterprises, Inc., Maarietta, GA (US)

(72) Inventors: Robert Blaskovic, Marietta, GA (US); Rudolfo Martinez, Santa Fe, NM (US); Nathan P Martinez, Santa Fe, NM (US); Cliffford J Unkefer, Los Alamos, NM (US)

( * ) Notice: Subject to any disclaimer, the term of this patent is extended or adjusted under 35 U.S.C. 154(b) by 104 days.

(21) Appl. No.: 17/322,521

(22) Filed: May 17, 2021

(65) Prior Publication Data

US 2022/0372002 A1  Nov. 24, 2022

(51) Int. Cl.
*C07D 237/04* (2006.01)
(52) U.S. Cl.
CPC ................... *C07D 237/04* (2013.01)
(58) Field of Classification Search
CPC .................................................. C07D 237/04
See application file for complete search history.

(56) References Cited

U.S. PATENT DOCUMENTS 7,074,959 B2 *  7/2006  Helvenston .............. A62D 3/30
544/239

OTHER PUBLICATIONS

Qian et al. (European J. of Med. Chem. 137 (2017) 598-611).*
NASA Report (2009).*
Byeongno Lee (Tetrahedron Letters 54 (2013) 1384-1388).*

* cited by examiner

*Primary Examiner* — Valerie Rodriguez-Garcia
(74) *Attorney, Agent, or Firm* — Ortiz & Lopez, PLLC; Kermit D. Lopez; Luis M. Ortiz

(57) ABSTRACT

A method for producing 6-oxo-1,4,5,6-tetrahydro-pyridazine-3-carboxylic acid is disclosed that includes steps of adding hydrazine sulfate with 2-ketoglutaric acid in a container as a solid, adding water to the solid creating a heterogenous mixture of the hydrazine sulfate, 2-ketoglutaric acid and water, blending the heterogenous mixture for at least one hour, and measuring the heterogenous mixture to confirm that it has converted into 6-oxo-1,4,5,6-tetrahydro-pyridazine-3-carboxylic acid. Hydrazine sulfate can be added to the 2-ketoglutaric acid in the container at a ratio of greater than 1.1. The compound 6-oxo-1,4,5,6-tetrahydro-pyridazine-3-carboxylic acid (PCA) has many uses. It has been used for medical applications and as a building block and for medical applications. The compound is also a product of the remediation of hydrazine using 2-ketogluraric acid.

3 Claims, 4 Drawing Sheets

300

| Reagent | MW | Amount | Moles | Eq | Amount Kg | |
|---|---|---|---|---|---|---|
| 2KG | 146.10 | 33684.29 | 230.56 | 1.20 | 33.68 | Kg |
| Hydrazine Sulfat | 130.12 | 25000.00 | 192.13 | 1.00 | 25.00 | Kg |
| PCA | 142.10 | 27301.72 | 192.13 | 1.00 | 27.30 | Kg |
| 1M | | 27.30 | Kg | | | |
| | Volume | 337.50 | Liters | 13.50 | | |
| | | 89.17 | Gallons | | | 1 Reaction |
| Sulfuric acid | 98.21 | 18869.12 | 192.13 | 1.00 | Molarity | 0.56927509 |
| | | 18.87 | | | | |
| Volume | | 472.5 | | | | |

| # Repeat Reactions | | 10 | | Amount | Amount Kg |
|---|---|---|---|---|---|
| | FW | Moles | Grams | | |
| 2KG | 146.10 | 2305.56 | 336842.91 | | 336.84 |
| HzSulfate | 130.12 | 1921.30 | 250000.00 | | 250.00 |
| PCA | 142.10 | 1921.30 | 273017.21 | | 273.02 |
| | | | | | |
| H2SO4 | 98.21 | 1921.30 | 188691.21 | | 188.69 |
| | | | | | |
| H2SO4 Molarity | 4.07 | | | | |
| | | | | | |

FIG. 4

SYNTHESIS OF 6-OXO-1,4,5,6-TETRAHYDROPYRIDIZIN-3-CARBOXYLIC ACID

TECHNICAL FIELD

Embodiments of the present invention generally related to 6-oxo-1,4,5,6-tetrahydropyridazine-3-carboxylic acid. More particularly, embodiments relate to the syntheses of 6-oxo-1,4,5,6-tetrahydropyridazine-3-carboxylic acid using hydrazine sulfate.

BACKGROUND

The compound 6-oxo-1,4,5,6-tetrahydropyridazine-3-carboxylic acid (PCA) has been used for medical applications and as a building block and for medical applications. The compound is also a product of the remediation of hydrazine using 2-ketogluraric acid. Hydrazine is volatile and highly flammable. Furthermore, present syntheses of the title compound require solvents or heat that add cost and handling hazards that would be best to avoid. What is needed are alternative, safer methods for producing 6-oxo-1,4,5,6-tetrahydropyridazine-3-carboxylic acid. Accordingly, the present inventors have developed the following synthesis to accomplish this goal.

SUMMARY OF THE EMBODIMENTS

The following summary is provided to facilitate an understanding of some of the features of the disclosed embodiments and is not intended to be a full description. A full appreciation of the various aspects of the embodiments disclosed herein can be gained by taking the specification, claims, drawings, and abstract as a whole.

It is a feature of the embodiments to provide a method for the safe commercial production of the 6-oxo-1,4,5,6-tetrahydropyridazine-3-carboxylic acid compound using hydrazine sulfate. Hydrazine sulfate is a solid and is less hazardous than hydrazine because it is nonvolatile and does not have the flammability problems of hydrazine. Prior efforts for the syntheses of 6-oxo-1,4,5,6-tetrahydropyridazine-3-carboxylic acid require solvents or heat that add cost and handling hazards that would be best to avoid.

According to an embodiment, hydrazine sulfate can be blended into (e.g., mixed, stirred, or blended with) 2-ketoglutaric acid within a container. To these solids water can be added and the heterogenous mixture can be blended. The mixture can be blended until the hydrazine level is measured and indicates a conversion to 6-oxo-1,4,5,6-tetrahydropyridazine-3-carboxylic acid.

According to an embodiment, hydrazine sulfate can be added at a ratio of 1 to 1.2 with 2-ketoglutaric acid to a container as a solid. To these solids water can be added and the heterogenous mixture can be blended. The mixture can be blended until the hydrazine level is measured and indicates a conversion to 6-oxo-1,4,5,6-tetrahydropyridazine-3-carboxylic acid.

In accordance with additional features of the embodiments, a method for producing 6-oxo-1,4,5,6-tetrahydropyridazine-3-carboxylic acid can include steps of adding hydrazine sulfate and 2-ketoglutaric acid together in a container as a solid, then adding water to the solid creating a heterogenous mixture of the hydrazine sulfate, 2-ketoglutaric acid and water. The heterogenous mixture can be blended until it is confirmed that it has converted into 6-oxo-1,4,5,6-tetrahydropyridazine-3-carboxylic acid.

In accordance with a feature of the embodiments, when blending the heterogenous mixture for about an hour, the temperature of the heterogenous mixture can be experienced to drop and then increase during blending before the heterogenous mixture is confirmed to have been converted into 6-oxo-1,4,5,6-tetrahydropyridazine-3-carboxylic acid.

In accordance with additional feature of the embodiments, a system for producing 6-oxo-1,4,5,6-tetrahydropyridazine-3-carboxylic acid can be provided that includes reaction tank, a powder funnel coupled to the reaction tank, three three-way valves A, B, and C for directing the flow of liquid, at least one pump for circulating liquid, a metering valve, a filter bag, and a filtrate tank.

In accordance with additional feature of the embodiments, the three-way valves A, B, and C can be set to blend liquids and compounds by circulating them out of the bottom of a reaction tank and back into the top of the reaction tank. The pump can be started after deionized water is added to the reaction tank. In Step 2, 2-ketoglutaric acid can be added into the reaction tank through the powder funnel. The 2-ketoglutaric acid and deionized water can then be circulated until it becomes blended into a solution. Then Hydrazine Sulfate can be added to the solution in powder form at the reaction tank using the powder funnel. It should be appreciated that the product can also be produced using this procedure with any concentration of hydrazine. The solution now with Hydrazine Sulfate can be allowed to circulate through the reaction tank for more than an hour. A reaction of the solution can then be checked for free hydrazine after it has been allowed to circulate. If the level is 5 ppm or less, the reaction can be considered to be complete. Three-way valve A can be set so flow of the solution can both return to the reaction tank and can also go into the filter bag. The metering valve can be used to limit the flow of liquid into the filter bag such that a portion of the flow can be returned to the reaction tank. This can keep the solid suspended and allow the filter bag to be filled slowly. After the filter bag is devoid of liquid, valves A, B and C can be set to flow the filtrated liquid back to the reaction tank, where then the filtrate can be moved into a reaction flask via an output port.

The compound 6-oxo-1,4,5,6-tetrahydropyridazine-3-carboxylic acid (PCA) has many uses. It has been used for medical applications and as a building block and for medical applications. The compound is also a product of the remediation of hydrazine using 2-ketogluraric acid.

These and other aspects of the embodiments will become more apparent in light of the detailed specification and drawings that follow.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 3 illustrates a table showing reaction amounts for one reaction for the synthesis, in accordance with the embodiments.

FIG. 4 illustrates a table of reaction amounts for ten reactions for the synthesis, in accordance with the embodiments.

DETAILED DESCRIPTION

Figure 1:
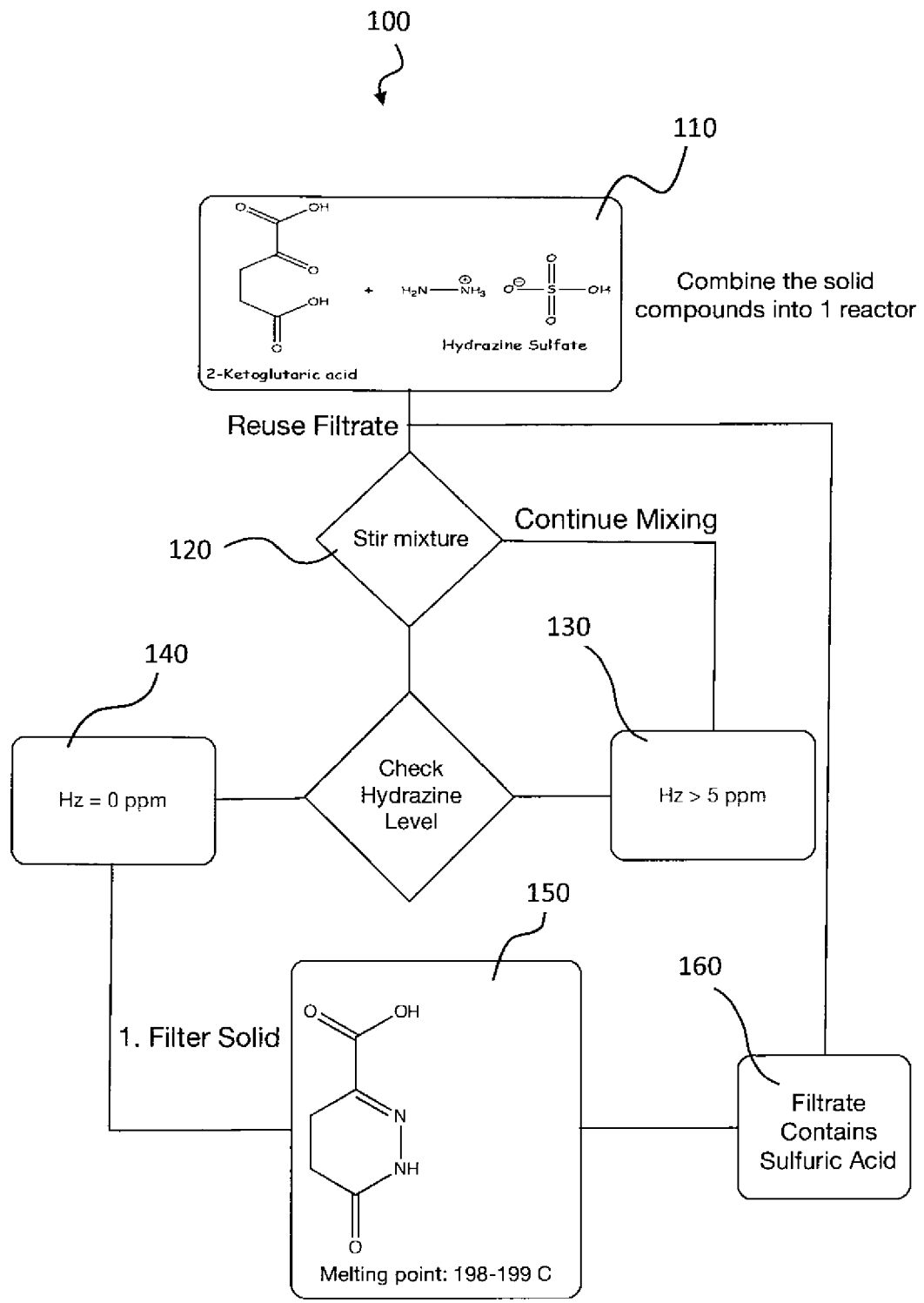
FIG. 1 illustrates a flow diagram of a process for producing 6-oxo-1,4,5,6-tetrahydropyridazine-3-carboxylic acid, in accordance with the embodiments.

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other issues, subject matter may be embodied as methods, devices, components, or systems. The following detailed description is, therefore, not intended to be interpreted in a limiting sense.

According to an embodiment, hydrazine sulfate can be blended into (e.g., mixed, stirred, or blended with) 2-ketoglutaric acid within a container. To these solids water can be added and the heterogenous mixture can continue to be blended. The mixture can be blended until the hydrazine level is measured and indicates a conversion to 6-oxo-1,4,5,6-tetrahydropyridazine-3-carboxylic acid.

According to another embodiment, hydrazine sulfate can be added at a ratio of 1 to 1.2 with 2-ketoglutaric acid to a container as a solid. To these solids water can be added and the heterogenous mixture can be stirred. The mixture can be stirred until the hydrazine level is measured and indicates a conversion to 6-oxo-1,4,5,6-tetrahydropyridazine-3-carboxylic acid.

Laboratory Example:

In an laboratory performed example, hydrazine sulfate of 105.08 g, 0.808 moles was combined with 2-ketoglutaric acid at 124.2 g, 0.987 moles (1.2 equivalents to the hydrazine sulfate) in a container, together creating a solid. To this solid, water at about 800 mL was added and the heterogenous mixture was stirred. A reaction started at 22° C. and the temperature of the mixture dropped to 14° C. over 2 minutes. After about one 1 hour, the reaction temperature returned to 22° C. The mixture was measured at 25 ppm after one hour of stirring. The reaction continued to be stirred overnight, and the mixture's hydrazine level was measured using a Chemetrics kit indicating that all hydrazine had been converted to 6-oxo-1,4,5,6-tetrahydropyridazine-3-carboxylic acid. The following reactions illustrate the above-described synthesis:

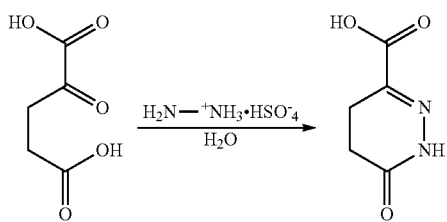

The product was filtered and then washed with water (at about 400 mL) which was added to the mixture by filter funnel. The product was collected and allowed to air dry. The total mass after air drying at ambient temperature was determined to be about 106.5 grams (93% yield). A melting point was determined at 198-199° C., which is equivalent to reported melting points for 6-oxo-1,4,5,6-tetrahydropyridazine-3-carboxylic acid. An additional benefit of this process is that the aqueous (Sulfuric Acid) can be reused up to 10 times to reduce the amount of waste that is produced for large scale production.

Referring to FIG. 1, illustrated is a flow diagram 100 of an exemplary process for producing 6-oxo-1,4,5,6-tetrahydropyridazine-3-carboxylic acid, in accordance with the embodiments. As shown in Block 110, the solid compounds of Hydrazine Sulfate and 2-Ketoglutaric acid are combined into a reactor. In Block 120, the mixture of the solid compounds is blended (e.g., mixed, stirred, blended) for a period of time. At Block 130, the hydrazine level of the blended compounds not in liquid form is checked. If the hydrazine level is greater than 5 ppm, then mixture of the liquid continues, as shown in Block 140. If the hydrazine level is found to be closer to 0 ppm (e.g., less than 5 ppm), then the liquid is filtered to arrive at the filtered compound shown in Block 150. As shown in Block 160, the filtrate can contain Sulfuric Acid, which can be reused, as shown between Block 110 and Block 120, with its reintroduction into the reactor.

Figure 2:
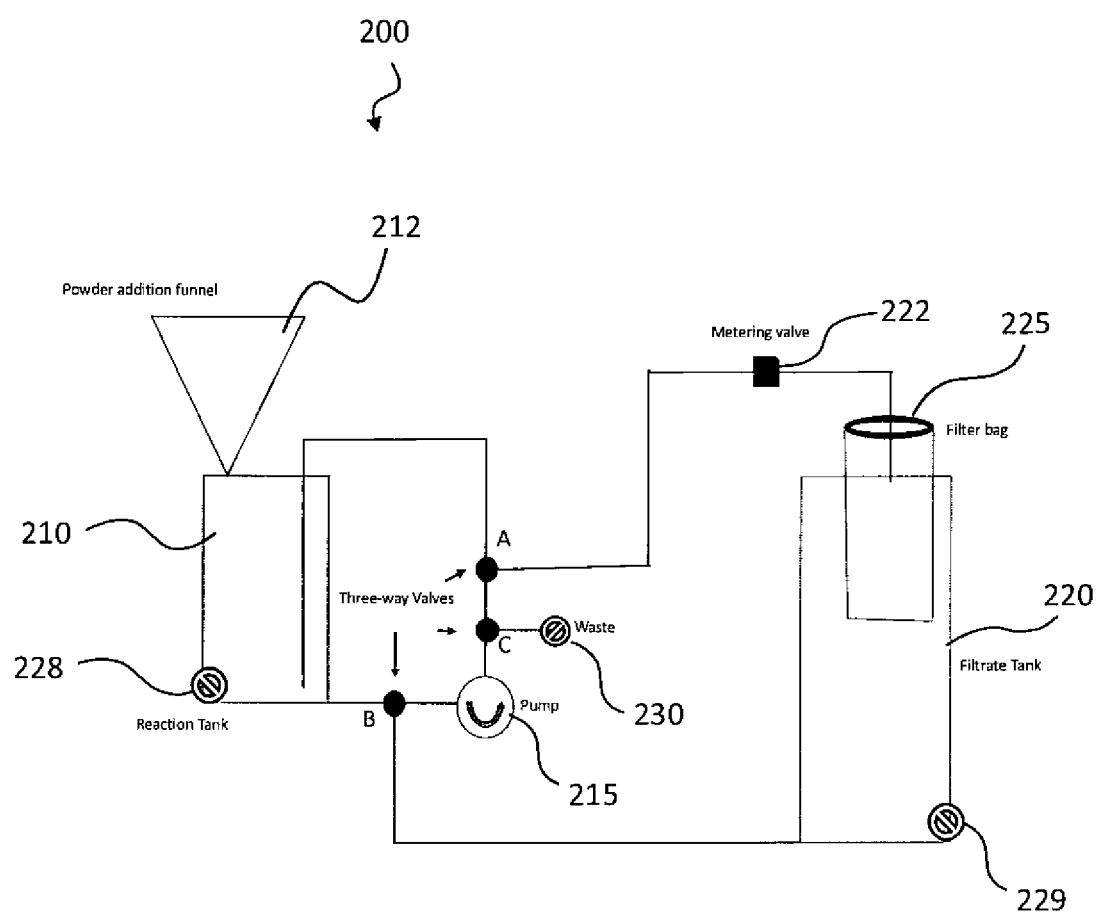
FIG. 2 illustrates a diagram of a system that can be used for producing 6-oxo-1,4,5,6-tetrahydropyridazine-3-carboxylic acid, in accordance with the embodiments.

Referring to FIG. 2, illustrated is a diagram of a system 200 that can be used for producing 6-oxo-1,4,5,6-tetrahydropyridazine-3-carboxylic acid, in accordance with the embodiments. The system 200 can include reaction tank 210, a powder funnel 212 coupled to the reaction tank 210, three three-way valves A, B, and C for directing the flow of liquid, and can also cause liquids and compounds to blend together, at least one pump 215 for circulating liquid, a metering valve 222, a filter bag 225, and a filtrate tank 220.

During operation, STEP 1 can involve the function where the three-way valves A, B, and C can be set to circulate liquid out of the bottom of the reaction tank 210 and back into the top of the reaction tank 210. The pump 215 can be started after deionized water (e.g., about 90 gallons) is added to the reaction tank 210. In Step 2, 2-ketoglutaric acid (e.g., about 33.68 Kg) can be added into the reaction tank 210 through the powder funnel 212. The 2-ketoglutaric acid and deionized water can then be circulated until (e.g., for about 10 minutes) it becomes blended into a solution. Then Hydrazine Sulfate (e.g., about 25 Kg) can be added to the solution in powder form at the reaction tank 210 using the powder funnel 212. It should be appreciated that the product can also be produced using this procedure with any concentration of hydrazine. In STEP 3, The solution now with Hydrazine Sulfate can be allowed to circulate through the reaction tank 210 for more than an hour (e.g., overnight). A reaction of the solution can then be checked for free hydrazine after it has been allowed to circulate. This check can be achieved using, for example, the CHEMetrics VACUettes Hydraine Kit 9K-5005A) on a sample of the solution. If the level is 5 ppm or less (after 5 minutes), the reaction can be considered to be complete. In STEP 4, three-way valve A can be set so flow of the solution can both return to the reaction tank 210 and can also go into the filter bag 225. The metering valve 222 can be used to limit the flow of liquid into the filter bag 225 such that a portion (e.g., 80% to 90%) of the flow can be returned to the reaction tank 210. This can keep the solid suspended and allow the filter bag 225 to be filled slowly. In STEP 5, after the filter bag 225 is devoid of liquid, valves A, B and C can be set to flow the filtrated liquid back to the reaction tank 210, where then the filtrate can be moved into a reaction flask via an output port 228. An output port 229 can also be located on the Filtrate tank 120 for liquid removal. A final step can include the addition of water (e.g., 50 gallons) to the top of the filter bag 225 to wash the system 100. The pump 215 can then move the filtrate back to the reaction tank 210, to a waste port 230. I can be appreciated that the waste port 230 could also serve as an output port to retrieve finished product rather than require the use of output ports 228/229.

Referring to FIG. 3, a table 300 is illustrated showing reaction amounts for one reaction for the following synthesis:

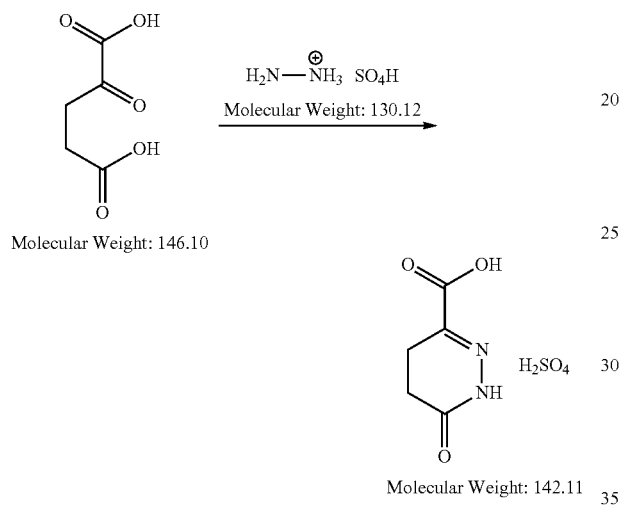

Table 300 essentially illustrates the typical reaction scale for the production of the desired product.

Referring to FIG. 4, a table 400 is illustrated showing reaction amounts for ten reactions for the same synthesis shown above. Table 400 illustrates the typical reaction sequence that will allow for the reduction of waste and therefore lower the overall cost of production. The solvent of the reaction can be recycled and used multiple times. The table illustrates the result for a 10 reaction production cycle.

It will be appreciated that variations of the above-disclosed embodiments and examples and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A method for producing 6-oxo-1,4,5,6-tetrahydro-pyridazine-3-carboxylic acid, comprising the steps of:
    providing a system including a reaction tank, a powder funnel coupled to the reaction tank, three three-way valves A, B, and C for directing the flow of liquid, at least one pump for circulating liquid, a metering valve, a filter bag, and a filtrate tank;
    set the three-way valves A, B, and C to circulate liquid out of the bottom of the reaction tank and back into the top of the reaction tank;
    add deionized water to the reaction tank and start the pump;
    add 2-ketoglutaric acid into the reaction tank through the powder funnel, wherein the 2-ketoglutaric acid and deionized water circulates until they become mixed into a solution;
    add hydrazine sulfate to the solution in powder form at the reaction tank using the powder funnel, wherein the solution with hydrazine sulfate added created a heterogenous mixture;
    allow the heterogenous mixture to circulate through the reaction tank for more than an hour;
    check a reaction level of the solution for free hydrazine after it has been allowed to circulate;
    if the reaction level is less than 5 ppm, the reaction is complete, otherwise continue with circulation through the reaction tank;
    if the reaction level is less than 5 ppm, set three-way valve A so flow of the solution both returns to the reaction tank and also partially goes into the filter bag and use a metering valve to limit flow of liquid into the filter bag such that a portion of the flow is returned to the reaction tank; and
    after the filter bag is devoid of liquid, valves A, B and C are set to flow filtrated liquid from the filtrate tank back to the reaction tank, where the solution as filtered can be moved into a reaction flask via an output port.

2. The method of claim 1, wherein the hydrazine sulfate is added at a ratio of 1 to 1.2 with the 2-ketoglutaric acid into the reaction tank via the powder funnel.

3. The method of claim 2, wherein the reaction level of the solution is checked for free hydrazine using a chemetrics kit.

* * * * *